(12) United States Patent
Dujmovic, Jr. et al.

(10) Patent No.: US 7,643,877 B2
(45) Date of Patent: Jan. 5, 2010

(54) CARDIAC RHYTHM MANAGEMENT SYSTEM WITH DEFIBRILLATION THRESHOLD PREDICTION

(75) Inventors: Richard Milon Dujmovic, Jr., Coon Rapids, MN (US); Phil Foshee, Woodinville, WA (US); Richard Fogoros, Pittsburg, PA (US); Joseph M. Smith, North Oaks, MN (US); Douglas R. Daum, Oakdale, MN (US); Weimin Sun, Thousand Oaks, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 537 days.

(21) Appl. No.: 11/061,315

(22) Filed: Feb. 18, 2005

(65) Prior Publication Data

US 2005/0251215 A1    Nov. 10, 2005

Related U.S. Application Data

(63) Continuation-in-part of application No. 09/808,419, filed on Mar. 14, 2001, now Pat. No. 6,751,502, which is a continuation of application No. 10/744,991, filed on Dec. 23, 2003, now Pat. No. 6,859,664, and a continuation-in-part of application No. 10/921,777, filed on Aug. 18, 2004, now Pat. No. 7,386,344.

(60) Provisional application No. 60/600,614, filed on Aug. 11, 2004.

(51) Int. Cl.
*A61N 1/08* (2006.01)
*A61N 1/39* (2006.01)
*A61N 1/365* (2006.01)

(52) U.S. Cl. .................... 607/8; 607/4; 607/5

(58) Field of Classification Search .................... 607/4, 607/5, 8

See application file for complete search history.

(56) References Cited

U.S. PATENT DOCUMENTS

RE30,372 E    8/1980    Mirowski et al.

(Continued)

FOREIGN PATENT DOCUMENTS

WO    WO-01/66180 A2    9/2001

(Continued)

OTHER PUBLICATIONS

"3 Abstracts from the Tenth Annual Scientific Congress of the Hong Kong College of Cardiology", *Medical Section*, 7(8), Jun. 21-23, 2002,(2002),11-13.

(Continued)

*Primary Examiner*—Carl H. Layno
*Assistant Examiner*—Tammie K. Heller
(74) *Attorney, Agent, or Firm*—Schwegman, Lundberg & Woessner, P.A.

(57) ABSTRACT

A cardiac rhythm management device predicts defibrillation thresholds without any need to apply defibrillation shocks or subjecting the patient to fibrillation. Intravascular defibrillation electrodes are implanted in a heart. By applying a small test energy, an electric field near one of the defibrillation electrodes is determined by measuring a voltage at a sensing electrode offset from the defibrillation electrode by a known distance. A desired minimum value of electric field at the heart periphery is established. A distance between a defibrillation electrodes and the heart periphery is measured, either fluoroscopically or by measuring a voltage at an electrode at or near the heart periphery. Using the measured electric field and the measured distance to the periphery of the heart, the defibrillation energy needed to obtain the desired electric field at the heart periphery is estimated. In an example, the device also includes a defibrillation shock circuit and a stimulation circuit.

12 Claims, 10 Drawing Sheets

U.S. PATENT DOCUMENTS

| | | |
|---|---|---|
| RE30,387 E | 8/1980 | Denniston, III et al. |
| 4,375,817 A | 3/1983 | Engle et al. |
| 4,693,253 A | 9/1987 | Adams |
| 4,727,877 A | 3/1988 | Kallok |
| 4,774,950 A | 10/1988 | Cohen |
| 4,799,493 A | 1/1989 | DuFault |
| 4,880,005 A | 11/1989 | Pless et al. |
| 4,960,123 A | 10/1990 | Maker |
| 4,986,270 A | 1/1991 | Cohen |
| 4,989,602 A | 2/1991 | Sholder et al. |
| 5,027,816 A | 7/1991 | Cohen |
| 5,048,521 A | 9/1991 | Pless et al. |
| 5,054,485 A | 10/1991 | Cohen |
| 5,083,563 A | 1/1992 | Collins |
| 5,085,213 A | 2/1992 | Cohen |
| 5,105,810 A | 4/1992 | Collins et al. |
| 5,111,816 A | 5/1992 | Pless et al. |
| 5,119,813 A | 6/1992 | Cohen |
| 5,190,034 A | 3/1993 | Sholder |
| 5,191,884 A | 3/1993 | Gilli et al. |
| 5,251,626 A | 10/1993 | Nickolls et al. |
| 5,257,621 A | 11/1993 | Bardy et al. |
| 5,269,300 A | 12/1993 | Kelly et al. |
| 5,311,874 A | 5/1994 | Baumann et al. |
| 5,312,443 A | 5/1994 | Adams et al. |
| 5,318,591 A | 6/1994 | Causey, III et al. |
| 5,318,597 A | 6/1994 | Hauck et al. |
| 5,325,856 A | 7/1994 | Nitzsche et al. |
| 5,336,253 A | 8/1994 | Gordon et al. |
| 5,350,401 A | 9/1994 | Levine |
| 5,350,406 A | 9/1994 | Nitzsche et al. |
| 5,354,316 A | 10/1994 | Keimel |
| 5,391,188 A | 2/1995 | Nelson et al. |
| 5,397,336 A | 3/1995 | Hirschberg et al. |
| 5,431,682 A | 7/1995 | Hedberg |
| 5,439,482 A | 8/1995 | Adams et al. |
| 5,531,770 A | 7/1996 | Kroll et al. |
| 5,540,724 A | 7/1996 | Cox |
| 5,554,174 A | 9/1996 | Causey, III |
| 5,584,868 A | 12/1996 | Salo et al. |
| 5,607,385 A | 3/1997 | Francischelli et al. |
| 5,662,687 A | 9/1997 | Hedberg et al. |
| 5,683,431 A | 11/1997 | Wang |
| 5,713,924 A | 2/1998 | Min et al. |
| 5,720,294 A | 2/1998 | Skinner |
| 5,722,994 A | 3/1998 | Noren et al. |
| 5,738,105 A | 4/1998 | Kroll |
| 5,749,901 A | 5/1998 | Bush et al. |
| 5,766,225 A | 6/1998 | Kramm |
| 5,782,879 A | 7/1998 | Rosborough et al. |
| 5,792,183 A | 8/1998 | Esler |
| 5,836,971 A | 11/1998 | Starkweather |
| 5,836,976 A | 11/1998 | Min et al. |
| 5,851,220 A | 12/1998 | Murphy |
| 5,857,977 A | 1/1999 | Caswell et al. |
| 5,868,793 A | 2/1999 | Nitzsche et al. |
| 5,873,897 A | 2/1999 | Armstrong et al. |
| 5,876,349 A | 3/1999 | Wang et al. |
| 5,882,352 A | 3/1999 | Duncan et al. |
| 5,885,221 A | 3/1999 | Hsu et al. |
| 5,891,170 A | 4/1999 | Nitzsche et al. |
| 5,916,238 A | 6/1999 | Hauser et al. |
| 5,925,067 A * | 7/1999 | Lu .............................. 607/28 |
| 5,931,857 A | 8/1999 | Prieve et al. |
| 5,951,592 A | 9/1999 | Murphy |
| 5,954,752 A | 9/1999 | Mongeon et al. |
| 5,978,700 A | 11/1999 | Nigam |
| 5,978,705 A | 11/1999 | KenKnight et al. |
| 5,999,852 A | 12/1999 | Elabbady et al. |
| 6,076,014 A | 6/2000 | Alt |
| 6,076,015 A | 6/2000 | Hartley et al. |
| 6,115,627 A | 9/2000 | Street |
| 6,128,529 A | 10/2000 | Esler |
| 6,151,524 A | 11/2000 | Krig et al. |
| 6,169,923 B1 | 1/2001 | Kroll |
| 6,212,428 B1 | 4/2001 | Hsu et al. |
| 6,223,078 B1 | 4/2001 | Marcovecchio |
| 6,230,055 B1 | 5/2001 | Sun et al. |
| 6,259,947 B1 | 7/2001 | Olson et al. |
| 6,269,267 B1 | 7/2001 | Bardy et al. |
| 6,275,732 B1 | 8/2001 | Hsu et al. |
| 6,317,632 B1 | 11/2001 | Krig et al. |
| 6,324,422 B1 | 11/2001 | Williams et al. |
| 6,327,499 B1 | 12/2001 | Alt |
| 6,353,761 B1 | 3/2002 | Conley et al. |
| 6,363,281 B1 * | 3/2002 | Zhu et al. ..................... 607/28 |
| 6,370,427 B1 | 4/2002 | Alt et al. |
| 6,393,316 B1 | 5/2002 | Gillberg et al. |
| 6,415,179 B1 | 7/2002 | Pendekanti et al. |
| 6,430,435 B1 | 8/2002 | Hsu et al. |
| 6,442,425 B1 | 8/2002 | Alt |
| 6,445,949 B1 | 9/2002 | Kroll |
| 6,449,503 B1 | 9/2002 | Hsu |
| 6,477,406 B1 | 11/2002 | Turcott |
| 6,484,055 B1 | 11/2002 | Marcovecchio |
| 6,487,443 B2 | 11/2002 | Olson et al. |
| 6,490,478 B1 | 12/2002 | Zhang et al. |
| 6,493,584 B1 | 12/2002 | Lu |
| 6,564,097 B1 | 5/2003 | Williams et al. |
| 6,567,691 B1 | 5/2003 | Stadler |
| 6,611,713 B2 | 8/2003 | Schauerte |
| 6,628,986 B1 | 9/2003 | Mouchawar et al. |
| 6,687,540 B2 | 2/2004 | Marcovecchio |
| 6,748,269 B2 | 6/2004 | Thompson et al. |
| 6,751,502 B2 | 6/2004 | Daum et al. |
| 6,754,527 B2 | 6/2004 | Stroebel et al. |
| 6,754,528 B2 | 6/2004 | Bardy et al. |
| 6,801,806 B2 | 10/2004 | Sun et al. |
| 6,859,664 B2 | 2/2005 | Daum et al. |
| 6,904,314 B1 | 6/2005 | Brewer et al. |
| 6,978,178 B2 | 12/2005 | Sommer et al. |
| 7,206,633 B2 | 4/2007 | Saba |
| 2001/0034539 A1 | 10/2001 | Stadler et al. |
| 2002/0002389 A1 | 1/2002 | Bradley et al. |
| 2002/0032469 A1 | 3/2002 | Marcovecchio |
| 2002/0035335 A1 | 3/2002 | Schauerte |
| 2002/0058968 A1 | 5/2002 | Sun et al. |
| 2002/0091333 A1 | 7/2002 | Hsu et al. |
| 2002/0107544 A1 | 8/2002 | Ostroff et al. |
| 2002/0123768 A1 | 9/2002 | Gilkerson |
| 2002/0133206 A1 | 9/2002 | Daum et al. |
| 2002/0169483 A1 | 11/2002 | Henry et al. |
| 2002/0188215 A1 | 12/2002 | Ferek-Petric |
| 2002/0188326 A1 | 12/2002 | Zheng et al. |
| 2003/0032989 A1 | 2/2003 | Herleikson |
| 2003/0045906 A1 | 3/2003 | Stroebel et al. |
| 2003/0060849 A1 | 3/2003 | Hsu |
| 2003/0074026 A1 | 4/2003 | Thompson et al. |
| 2003/0088282 A1 | 5/2003 | Ostroff |
| 2003/0097153 A1 | 5/2003 | Bardy et al. |
| 2003/0105491 A1 | 6/2003 | Gilkerson et al. |
| 2003/0120316 A1 | 6/2003 | Spinelli et al. |
| 2003/0144700 A1 | 7/2003 | Brown et al. |
| 2003/0195569 A1 | 10/2003 | Swerdlow et al. |
| 2003/0204209 A1 | 10/2003 | Burnes et al. |
| 2003/0204210 A1 | 10/2003 | Ousdigian et al. |
| 2003/0216654 A1 | 11/2003 | Xu et al. |
| 2004/0111121 A1 | 6/2004 | Brown et al. |
| 2004/0138714 A1 | 7/2004 | Daum et al. |
| 2006/0036288 A1 | 2/2006 | Bocek et al. |
| 2007/0043395 A1 | 2/2007 | Wei et al. |

2008/0249581 A1   10/2008   Wei

FOREIGN PATENT DOCUMENTS

| WO | WO-2006/020791 A1 | 2/2006 |
|---|---|---|
| WO | WO-2007/024471 A1 | 3/2007 |
| WO | WO-2008/123902 | 10/2008 |

OTHER PUBLICATIONS

"U.S. Appl. No. 10/921,777, Amendment and Response filed Jan. 9, 2008 to Final Office Action mailed Jul. 9, 2007", 19 pgs.

"U.S. Appl. No. 10/921,777, Amendment and Response filed Nov. 20, 2006 to Non-Final Office Action mailed Oct. 12, 2006", 24 pgs.

"U.S. Appl. No. 10/921,777, Final Office Action mailed Jul. 9, 2007", 8 pgs.

"U.S. Appl. No. 10/921,777, Non-Final Office Action mailed Oct. 12, 2006", 9 pgs.

"U.S. Appl. No. 10/921,777, Notice of Allowance mailed Feb. 1, 2008", 4 pgs.

"International Search Report and Written Opinion for Application No. PCT/US2005/028592, date mailed Jan. 19, 2006", 18 pgs.

Albert, C. M., et al., "Prospective Study of Sudden Cardiac Death Among Women in the United States", *Circulation*, 107, (2003), 2096-2101.

Bessho, R., et al., "Measurement of the Upper Limit of Vulnerability During Defibrillator Implantation can Substitute Defibrillation Threshold Measurement", *The International Journal of Artificial Organs*, 21 (3), (Mar. 1998), 151-160.

Boecker, D., et al., "Benefit of an Enhanced Detection Algorithm in Optimizing Treatment of Slow Ventricular Tachycardia", *Journal of Pacing and Clinical Electrophysiology*, 23 (Part II), (Abstract 95), (Apr. 2000), p. 576.

Buxton, A. E., et al., "Relation of Ejection Fraction and Inducible Ventricular Tachycardia to Mode of Death in Patients With Coronary Artery Disease—An Analysis of Patients Enrolled in the Multicenter Unsustained Tachycardia Trial", *Circulation*, 106, (2002), 2466-2472.

Chung-Seung, C., "Medical Session—Management of Congestive Heart Failure", *Medical Section*, 7(8), (2002), 4-9.

Church, T., et al., "A Model to Evaluate Alternative Methods of Defibrillation Threshold Determination", *Pace*, 11, (1988), 2002-2007.

Copie, X., et al., "Predictive Power of Increased Heart Rate Versus Depressed Left Ventricular Ejection Fraction and Heart Rate Variability for Risk Stratification After Myocardial Infarction", *Journal of the American College of Cardiology*, 27(2), (1996), 270-276.

Darpo, B., et al., "Incidence of Sudden Death After Radiofrequency Ablation of the Atrioventricular Junction for Atrial Fibrillation", *The American Journal of Cardiology*, 80, (1997), 1174-1177.

Dodinot, B., et al., "La Mort Subite Chez le Porteur de Stimulateur Cardiaque", *Annales de Cardiologie et D'Angeiologie*, (W/ English Summary), (1985), 161-166.

Eason, J., et al., "Influence of Anisotropy on Local and Global Measures of Potential Gradient in Computer Models of Defibrillation", *Annals of Biomedical Engineering*, 26, (1998), 840-849.

Ellenbogen, K. A., et al., "Immediate Reproducibility of Upper Limit of Vulnerability Measurements in Patients Undergoing Transvenous Implantable Cardioverter Defibrillator Implantation", *Journal of Cardiovascular Electrophysiology*, 9 (6), (Jun. 1998), 588-595.

Engdahl, J., et al., "The Epidemiology of Out-of-Hospital 'Sudden' Cardiac Arrest", *Resuscitation*, 52, (2002), 235-245.

Ezekowitz, J. A., et al., "Implantable Cardioverter Defibrillators in Primary and Secondary Prevention: A Systematic Review of Randomized, Controlled Trials", *Annals of Internal Medicine*, 138 (2003),445-452.

Fromer, M., et al., "Experience with a New Implantable Pacer-, Cardioverter-Defibrillator for the Therapy of Recurrent Sustained Ventricular Tachyarrhythmias: A Step Toward a Universal Ventricular Tachyarrhythmia Control Device", *Journal of Pacing and Clinical Electrophysiology*, 14,(1991),1288-1297.

Furman, S., "The Future of the Pacemaker", *Journal of Pacing and Clinical Electrophysiology*, 25(1), (2002),1-2.

Gasparini, M., et al., "Long-Term Follow-Up After Atrioventricular Nodal Ablation and Pacing: Low Incidence of Sudden Cardiac Death", *The Journal of Pacing and Clinical Electrophysiology*, 23 (11)(Part II), (2000),1925-1929.

Geelen, P., et al., "The Value of DDD Pacing in Patients with an Implantable Carioverter Defibrillator", *Journal of Pacing and Clinical Electrophysiology*, 20 (Part II), (1997),177-181.

Golino, A., et al., "Clinical Experience with the Transvenous Medtronic Pacer Cardioverter Defibrillator (PCD®) System", *Texas Heart Institute Journal*, 20(4), (1993), 264-270.

Gregoratos, G., et al., "ACC/AHA/NASPE 2002 Guideline Update for Implantation of Cardiac Pacemakers and Antiarrhythmia Devices: Summary Article—A Report of the American College of Cardiology/American Heart Association Task Force on Practice Guidelines", *Journal of Cardiovascular Electrophysiology*, 13(11), (ACC/AHA/NASPE Committee to Update the 1988 Pacemaker Guidelines),(2002), 1183-1199.

Grimm, W., et al., "Electrocardiographically Documented Unnecessary, Spontaneous Shocks in 241 Patients With Implantable Cardioverter Defibrillators", *Journal of Pacing and Clinical Electrophysiology*, 15(11)(Part 1), (1992), 1667-1673.

Higgins, S. L., et al., "Indications for Implantation of a Dual-Chamber Pacemaker Combined With an Implantable Cardioverter-Defibrillator", *American Journal of Cardiology*, 81(11), (1998), 1360-1362.

Hohnloser, S. H., et al., "Changing Late Prognosis of Acute Myocardial Infarction—Impact on Management of Ventricular Arrhythmias in the Era of Reperfusion and the Implantable Cardioverter-Defibrillator", *Circulation*, 107, (2003), 941-946.

Ideker, R. E., "Chapter 2—Mechanisms of Defibrillation", *Defibrillation of the Heart : ICDs, AEDs, and Manual*, St. Louis : Mosby,(1994), 15-45.

Iskos, D., et al., "Physiological Cardiac Pacing in Patients With Contemporary Implantable Cardioverter-Defibrillators", *American Journal of Cardiology*, 82(1), (1998), 66-71.

Jouven, X., et al., "Predicting Sudden Death in the Population—The Paris Prospective Study I", *Circulation*, 99, (1999),1978-1983.

Kanagaratnam, L., et al., "Matching Approved "Nondedicated" Hardware to Obtain Biventricular Pacing and Defibrillation: Feasibility and Troubleshooting", *Journal of Pacing and Clinical Electrophysiology*, 25(7), (2002), 1066-1071.

Kay, G. N., et al., "The Abate and Pace Trial: A Prospective Study of Catheter Ablation of the AV Conduction System and Permanent Pacemaker Implantation for Treatment of Atrial Fibrillation", *Journal of Interventional Cardiac Electrophysiology*, 2(2), (1998),121-135.

Lamas, G. A., et al., "The Mode Selection Trial (MOST) in Sinus Node Dysfunction: Design, Rationale, and Baseline Characteristics of the First 1000 Patients", *American Heart Journal*, 140, (2000), 541-551.

Lavergne, T., et al., "Preliminary Clinical Experience with the First Dual Chamber Pacemaker Defibrillator", *Journal of Pacing and Clinical Electrophysiology*, 20(1) (Part II), (1997),182-188.

Liu, B. C., et al., "Inappropriate Shock Delivery and Biventricular Pacing Cardiac Defibrillators", *Texas Heart Journal*, 30(1), (2003),45-49.

Martin, D. J., et al., "Upper Limit of Vulnerability Predicts Chronic Defibrillation Threshold for Transvenous Implantable Defibrillators", *Journal of Cardiovascular Electrophysiology*, 8 (3), (Mar. 1997),241-248.

Mattioli, A. V., et al., "Causes of Death in Patients with Unipolar Single Chamber Ventricular Pacing: Prevalence and Circumstances in Dependence on Arrhythmias Leading to Pacemaker Implantation", *Journal of Pacing and Clinical Electrophysiology*, 18(1)(Part 1), (1995),11-17.

Min, X., et al., "Finite element analysis of defibrillation fields in a human torso model for ventricular defibrillation", *Progress in Biophysics & Molecular Biology*, 69, (1998), 353-386.

Morris, M. M., et al., "A Preview of Implantable Cardioverter Defibrillator Systems in the Next Millennium: An Integrative Cardiac Rhythm Management Approach", *American Journal of Cardiology*, 83 (5B), (1999), 48D-54D.

Myerburg, R. J., et al., "Opportunities for Sudden Death Prevention: Directions for New Clinical and Basic Research", *Cardiovascular Research*, 50, (2001),177-185.

Pendekanti, R., et al., "Spatial Potential and Current Distributions Along Transvenous Defibrillation Electrodes: Variation of Electrode Characteristics", *Annals of Biomedical Engineering*, 24, (1996),156-167.

Pinski, S. L., et al., "Permanent Pacing via Implantable Defibrillators", *Journal of Pacing and Clinical Electrophysiology*, 23 (11 Part 1), (2000),1667-1682.

Saksena, S., et al., "Long-Term Multicenter Experience With a Second-Generation Implantable Pacemaker-Defibrillator in Patients With Malignant Ventricular Tachyarrhythmias", *Journal of American College of Cardiology*, 19(3), (1992), 490-499.

Santini, M., et al., "Indications for Dual-Chamber (DDD) Pacing in Implantable Cardioverter-Defibrillator Patients", *American Journal of Cardiology*, 78(Supp. 5A), (1996), 116-118.

Schimpf, P. H., et al., "Effects of electrode interface impedance of finite element models of transvenous defibrillation", *Medical & Biological Engineering & Computing*, (1995), 713-719.

Singer, I., et al., "The Initial Clinical Experience with an Implantable Cardioverter Defibrillator/Antitachycardia Pacemaker", *Journal of Pacing and Clinical Electrophysiology*, 14, (1991),1119-1128.

Sun, W., et al., "DFT Test Via Pacing Measurements without VF Induction and Shocking", *PACE*, vol. 23, (Abstract No. 235), (2000), 1 pg.

Sweeney, M. O., et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction", *Circulation*, 107(23), (2003), 2932-2937.

Swerdlow, C. D., et al., "Comparative Reproducibility of Defibrillation Threshold and Upper Limit of Vulnerability", *PACE*, 19, (1996), 2103-2111.

Swerdlow, C. D., et al., "Programming of Implantable Cardioverter-Defibrillators on the Basis of the Upper Limit of Vulnerability", *Circulation*, 95 (6), (1997), 1497-1504.

Thackray, S. D., et al., "The Prevalence of Heart Failure and Asymptomatic Left Ventricular Systolic Dysfunction in a Typical Regional Pacemaker Population", *European Heart Journal*, 24, (2003), 1143-1152.

Twidale, N., et al., "Predictors of Outcome After Radiofrequency Catheter Ablation of the Atrioventricular Node for Atrial Fibrillation and Congestive Heart Failure", *American Heart Journal*, 136(4)(Part 1), (1998), 647-657.

Wang, Y., et al., "Analysis of Defibrillation Efficacy from Myocardial Voltage Gradients with Finite Element Modeling", *IEEE Transactions on Biomedical Engineering*, 46 (9), (1999), 1025-1036.

Zehender, M., et al., "Prevalence, Circumstances, Mechanisms, and Risk Stratification of Sudden Cardiac Death in Unipolar Single-Chamber Ventricular Pacing", *Circulation*, 85, (1992), 596-605.

"U.S. Appl. No. 09/808,419, Amendment and Response filed Dec. 6, 2002 to Non-Final Office Action mailed Sep. 10, 2002", 14 pgs.

"U.S. Appl. No. 09/808,419, Non-Final Office Action mailed Jul. 16, 2003", 7 pgs.

"U.S. Appl. No. 09/808,419, Non-Final Office Action mailed Sep. 10, 2002", 7 pgs.

"U.S. Appl. No. 09/808,419, Notice of Allowance mailed Jan. 17, 2003", 8 pgs.

"U.S. Appl. No. 09/808,419, Notice of Allowance mailed Feb. 26, 2004", 6 pgs.

"U.S. Appl. No. 10/744,991, Notice of Allowance mailed Sep. 21, 2004", 7 pgs.

"U.S. Appl. No. 11/208,923, Response filed Jan. 21, 2009 to Non Final Office Action mailed Sep. 17, 2008", 16 pgs.

"U.S. Appl. No. 11/208,923 Non-Final Office Action mailed Sep. 17, 2008.", 10 pgs.

"International Application No. PCT/US2008/001637, International Search Report mailed Jul. 9, 2008", 5 pgs.

"International Application Serial No. PCT/US2008/001637, Written Opinion mailed Jul. 9, 2008", 8 pgs.

"European Application Serial No. 06789564.9, Office Action mailed Jul. 15, 2008", 4 pgs.

\* cited by examiner

DEFIBRILLATION THRESHOLD VOLTAGE LOOKUP TABLE
(VOLTS)

D2-D1 (CM)

| FRACTIONAL TIP VOLTAGE PARAMETER | 1 | 1.2 | 1.4 | 1.6 | 1.8 | 2 | 2.2 | 2.4 | 2.6 | 2.8 | 3 | 3.2 | 3.4 | 3.6 | 3.8 | 4 | 4.2 | 4.4 | 4.6 | 4.8 | 5 |
|---|---|---|---|---|---|---|---|---|---|---|---|---|---|---|---|---|---|---|---|---|---|
| 30.0 | 113 | 131 | 142 | 159 | 181 | 194 | 215 | 239 | 257 | 280 | 304 | 327 | 353 | 377 | 403 | 432 | 457 | 488 | 520 | 552 | 590 |
| 32.5 | 115 | 132 | 144 | 161 | 182 | 197 | 217 | 240 | 258 | 281 | 304 | 327 | 353 | 377 | 403 | 432 | 457 | 488 | 520 | 552 | 590 |
| 35.0 | 117 | 134 | 148 | 165 | 185 | 201 | 221 | 243 | 262 | 284 | 307 | 331 | 356 | 380 | 407 | 434 | 461 | 491 | 522 | 553 | 591 |
| 37.5 | 121 | 137 | 153 | 170 | 189 | 207 | 227 | 248 | 269 | 291 | 314 | 338 | 363 | 388 | 415 | 442 | 470 | 499 | 530 | 561 | 593 |
| 40.0 | 126 | 141 | 159 | 176 | 195 | 215 | 235 | 256 | 278 | 301 | 324 | 349 | 374 | 400 | 428 | 455 | 484 | 514 | 545 | 576 | 604 |
| 42.5 | 131 | 147 | 166 | 184 | 203 | 224 | 245 | 266 | 290 | 313 | 337 | 363 | 389 | 416 | 445 | 473 | 504 | 534 | 566 | 598 | 624 |
| 45.0 | 137 | 154 | 174 | 193 | 213 | 235 | 257 | 279 | 304 | 328 | 353 | 381 | 408 | 436 | 467 | 496 | 529 | 561 | 594 | 627 | 653 |
| 47.5 | 145 | 162 | 183 | 203 | 224 | 248 | 271 | 294 | 321 | 347 | 373 | 402 | 431 | 461 | 493 | 525 | 559 | 593 | 628 | 664 | 693 |
| 50.0 | 153 | 171 | 194 | 215 | 237 | 262 | 287 | 312 | 341 | 368 | 396 | 427 | 458 | 490 | 524 | 558 | 595 | 631 | 669 | 708 | 740 |
| 52.5 | 162 | 182 | 205 | 228 | 252 | 278 | 306 | 332 | 363 | 392 | 422 | 455 | 489 | 523 | 560 | 596 | 636 | 676 | 717 | 759 | 797 |
| 55.0 | 172 | 194 | 218 | 243 | 269 | 296 | 326 | 355 | 387 | 419 | 452 | 487 | 524 | 561 | 600 | 640 | 682 | 726 | 771 | 817 | 864 |
| 57.5 | 183 | 207 | 232 | 259 | 288 | 315 | 348 | 380 | 414 | 449 | 485 | 522 | 563 | 602 | 645 | 689 | 734 | 782 | 832 | 883 | 940 |
| 60.0 | 195 | 222 | 247 | 276 | 308 | 337 | 373 | 408 | 444 | 482 | 521 | 561 | 606 | 649 | 694 | 743 | 790 | 845 | 899 | 955 | 1025 |
| 62.5 | 208 | 237 | 263 | 295 | 330 | 359 | 399 | 439 | 476 | 518 | 560 | 604 | 653 | 699 | 748 | 802 | 853 | 913 | 973 | 1035 | 1119 |
| 65.0 | 221 | 254 | 280 | 315 | 354 | 384 | 428 | 471 | 510 | 556 | 603 | 649 | 704 | 754 | 806 | 866 | 920 | 987 | 1053 | 1122 | 1223 |
| 67.5 | 236 | 272 | 298 | 336 | 379 | 410 | 458 | 507 | 548 | 598 | 649 | 699 | 759 | 813 | 869 | 935 | 993 | 1067 | 1140 | 1217 | 1336 |
| 70.0 | 251 | 292 | 317 | 359 | 407 | 438 | 491 | 545 | 587 | 642 | 698 | 752 | 818 | 876 | 937 | 1009 | 1071 | 1154 | 1234 | 1318 | 1458 |

FIG. 3

CARDIAC RHYTHM MANAGEMENT SYSTEM WITH DEFIBRILLATION THRESHOLD PREDICTION

CROSS-REFERENCE TO RELATED APPLICATION(S)

This application is a continuation-in-part of U.S. patent application Ser. No. 10/744,991, filed on Dec. 23, 2003, now issued as U.S. Pat. No. 6,859,664, which is a continuation of U.S. patent application Ser. No. 09/808,419, filed on Mar. 14, 2001, now issued as U.S. Pat. No. 6,751,502 and is a continuation-in-part of U.S. patent application Ser. No. 10/921,777, filed Aug. 18, 2004, now issued as U.S. Pat. No. 7,386,344. This application also claims priority to Bocek et al. U.S. Provisional Patent Application Ser. 60/600,614, filed Aug. 11, 2004, entitled PACEMAKER WITH COMBINED DEFIBRILLATOR TAILORED FOR BRADYCARDIA PATIENTS. The above patent and patent applications are incorporated by reference in their entirety.

TECHNICAL FIELD

The present system relates generally to cardiac rhythm management systems and particularly, but not by way of limitation, to a system providing, among other things, defibrillation threshold prediction.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the determination of the threshold energy required, for a particular defibrillation shock waveform, to reliably convert a tachyarrhythmia into a normal heart rhythm. Ventricular and atrial fibrillation are probabilistic phenomena that observe a dose-response relationship with respect to shock strength. The ventricular defibrillation threshold (VDFT) is the smallest amount of energy that can be delivered to the heart to reliably revert ventricular fibrillation to a normal rhythm. Similarly, the atrial defibrillation threshold (ADFT) is the threshold amount of energy that will terminate an atrial fibrillation. Such defibrillation thresholds vary from patient to patient, and may even vary within a patient depending on the placement of the electrodes used to deliver the therapy. In order to ensure the efficacy of such therapy and to maximize the longevity of the battery source of such therapy energy, the defibrillation thresholds must be determined so that the defibrillation energy can be safely set above the threshold value but not at so large of a value so as to waste energy and shorten the usable life of the implanted device.

One technique for determining the defibrillation threshold is to induce the targeted tachyarrhythmia (e.g., ventricular fibrillation), and then apply shocks of varying magnitude to determine the energy needed to convert the arrhythmia into a normal heart rhythm. However, this requires imposing the risks and discomfort associated with both the arrhythmia and the therapy. Electrical energy delivered to the heart has the potential to both cause myocardial injury and subject the patient to pain. Moreover, if defibrillation thresholds are being obtained in order to assist the physician in determining optimal lead placement, these disadvantages are compounded as the procedure is repeated for different potential lead placements.

Another technique for determining the defibrillation threshold, referred to as the "upper limit of vulnerability" technique, a patient in a state of normal heart rhythm is shocked during the vulnerable (T-wave) period of the cardiac cycle during which time the heart tissue is undergoing repolarization. Shocks of varying magnitude are applied until fibrillation is induced. Of course, after such fibrillation is induced, the patient must be again shocked in order to interrupt the arrhythmia and reestablish a normal heart rhythm. In this technique, the corresponding fibrillation-inducing shock magnitude is then related to a defibrillation threshold energy using a theoretical model. The upper limit of vulnerability technique also suffers from imposing the risks and discomfort associated with both the arrhythmia and the shock therapy. Moreover, because of the discomfort associated with the fibrillation and countershocks, the patient is typically sedated under general anesthesia, which itself has some additional risk and increased health care cost. For these and other reasons, there is a need to estimate defibrillation thresholds without relying on a defibrillation shock to induce or terminate an actual arrhythmia.

SUMMARY

The present system provides, among other things, a cardiac rhythm management system that predicts defibrillation thresholds without any need to apply defibrillation shocks or subjecting the patient to fibrillation. In one embodiment, the system provides a method that includes delivering a non-defibrillating and nonfibrillation-inducing test energy to a heart, detecting a resulting output signal based on the test energy and a heart characteristic, and estimating a defibrillation threshold, based on the output signal, for a portion of the heart to be defibrillated. In an embodiment, a method also includes detecting at least one intrinsic electrical heart signal from a heart of a patient and delivering to the heart a stimulation at an energy level appropriate to evoke or assist in evoking a responsive heart contraction. In an embodiment, the method also includes detecting a ventricular tachyarrhythmia or fibrillation using a technique having a specificity and a sensitivity, wherein the specificity exceeds the sensitivity, and delivering a shock in response to at least the detected tachyarrhythmia or fibrillation, the shock in excess of the threshold voltage associated with the second electric field strength.

In one embodiment, the system includes first and second electrodes configured for association with a heart. A test energy module is coupled to the second electrode, for delivering a nondefibrillating and nonfibrillation-inducing test energy to the heart. A response signal module is coupled to the first and second electrodes for detecting responses to the test energy. A controller is coupled to the response signal module. The controller estimates a defibrillation threshold energy based on a predetermined desired defibrillation electric field at a distal portion of the heart tissue to be defibrillated and a distance from the second electrode to the distal portion of the heart tissue, and an indication of the electric field near the second electrode. Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 3 is a lookup table illustrating estimating defibrillation threshold voltages based on an indication of electric field near a defibrillation electrode and a distance therefrom.

DETAILED DESCRIPTION

Figure 1:
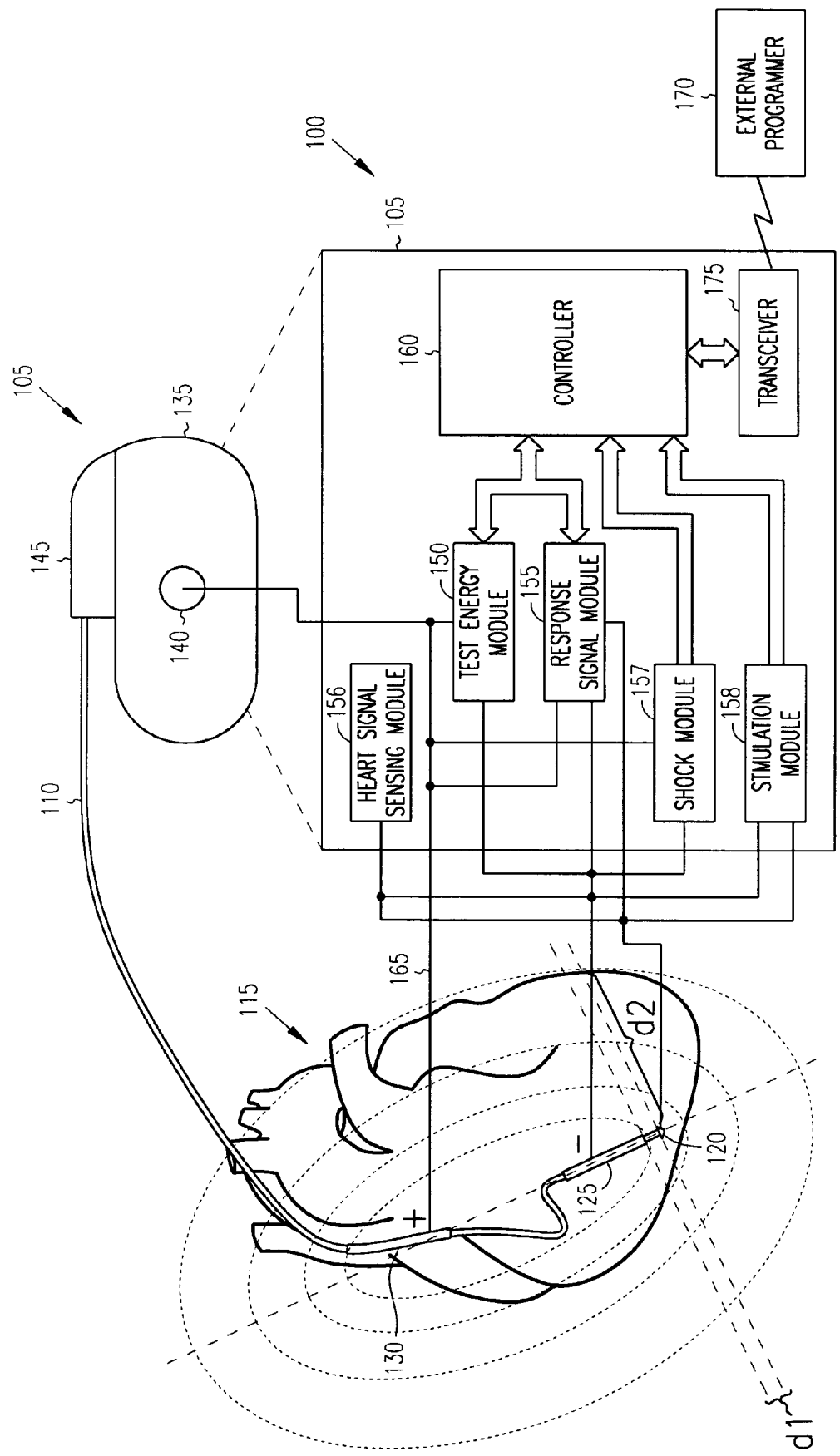
FIG. 1 is a schematic/block diagram illustrating portions of the present cardiac rhythm management system and portions of an environment of use.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. The term "and/or" refers to a nonexclusive "or" (i.e., "A and/or B" includes both "A and B" as well as "A or B").

The present methods and apparatus will be described in applications involving implantable medical devices including, but not limited to, implantable cardiac rhythm management systems such as pacemakers, cardioverter/defibrillators, pacer/defibrillators, biventricular or other multi-site coordination devices, and drug delivery systems for managing cardiac rhythm. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

EXAMPLE A

FIG. 1 is a schematic/block diagram illustrating generally, by way of example, and not by way of limitation, one embodiment of portions of the present cardiac rhythm management system 100 and portions of an environment in which the present system 100 and associated techniques are used. System 100 includes, among other things, cardiac rhythm management device 105 and leadwire ("lead") 110 for communicating signals between device 105 and a portion of a living organism, such as heart 115. Embodiments of device 105 include, but are not limited to, bradycardia and antitachycardia pacemakers, cardioverters, defibrillators, combination pacemaker/defibrillators, drug delivery devices, and any other implantable or external cardiac rhythm management apparatus capable of providing therapy to heart 115.

In this example, lead 110 includes multiple electrodes, and individual conductors for independently communicating an electrical signal from each electrode to device 105. In one embodiment, these electrodes include a right ventricular (RV) tip-type electrode 120 at the distal end of lead 110. In one example embodiment, electrode 120 has a macroscopic surface area that is approximately between 1 mm$^2$ and 20 mm$^2$, inclusive. RV tip electrode 120 is configured to be positioned in the right ventricle at or near its apex or at any other suitable location. RV shock electrode 125 is located on the lead at a known predetermined distance, d1, from RV tip electrode 120, as measured from the edges of these electrodes. RV shock electrode 125 is typically located in the right ventricle or at any other suitable location. In one embodiment, RV shock electrode 125 is a coil-type electrode having a macroscopic surface area that is approximately between 2 cm$^2$ and 20 cm$^2$, inclusive. Superior vena cava (SVC) electrode 130 is located in a portion of the superior vena cava, the right atrium, or both, or at any other suitable location. In one embodiment, SVC electrode 130 is a coil-type electrode having a macroscopic surface area that is approximately between 2 cm$^2$ and 20 cm$^2$, inclusive. Although RV tip electrode 120, RV shock electrode 125, and SVC electrode 130 are particularly described above with respect to structural characteristics and locations for disposition, it is understood that these electrodes may take the form of any of the various cardiac electrodes known in the art (e.g., epicardial patch electrodes) and may be positioned elsewhere for association with heart 115 or other tissue.

In one embodiment, device 105 includes a hermetically sealed housing 135, formed from a conductive metal, such as titanium, and implanted within a patient such as within the pectoral or abdominal regions. In this example, housing 135 (also referred to as a "case" or "can") is substantially covered over its entire surface by a suitable insulator, such as silicone rubber, except for at a window that forms a "case" or "can" or "housing" electrode 140. As understood by one of ordinary skill in the art, housing electrode 140, although not located in the heart, is associated with the heart for providing what is sometimes referred to as "unipolar" sensing or pacing or defibrillation therapy. In one embodiment, a header 145 is mounted on housing 135, such as for receiving lead 110. Header 145 is formed of an insulative material, such as molded plastic. Header 145 also includes at least one receptacle, such as for receiving lead 110 and electrically coupling conductors of lead 110 to device 105. Header 145 may also include one or more additional electrodes. In this example, ventricular fibrillation is treated by delivering a defibrillation shock between RV shock electrode 125 and the commonly connected combination of SVC electrode 130 and housing electrode 140; a defibrillation threshold is also obtained with SVC electrode 130 and housing electrode 140 connected in common. However, it is understood that these electrodes could be differently configured, such as for delivering defibrillation therapy between RV shock electrode 125 and housing electrode 140.

FIG. 1 also illustrates, in an exploded view block diagram form, portions of device 105. It is understood that device 105 is coupled to heart 115 via lead 110; the illustrated connection lines associated with the exploded view are illustrative only. In FIG. 1, test energy module 150 generates an energy from which a heart characteristic can be determined via response signal module 155. From these measurements, a defibrillation threshold is computed, for example, either by a defibrillation threshold estimation module in controller 160, which itself is in device 105, or in external programmer 170, which is communicatively coupled to a transmitter or receiver in device 105, such as transceiver 175. The defibrillation estimation module is implemented as a sequence of steps carried out on a microprocessor or other microsequencer, in analog, digital, or mixed-signal hardware, or in any suitable hardware and/or software configuration. In this example, SVC electrode 130 is electrically connected in common with housing electrode 140, at node 165, and also coupled to each of test energy module 150 and response signal module 155. The device 105 also includes a heart signal sensing module 156, a defibrillation shock module 157, and a stimulation module 158. In an example, the test energy module 150 includes at least a portion of the shock module 157 or the stimulation module 158. In another example, the response signal module 155 includes at least a portion of the heart signal sensing module 156.

Figure 2:
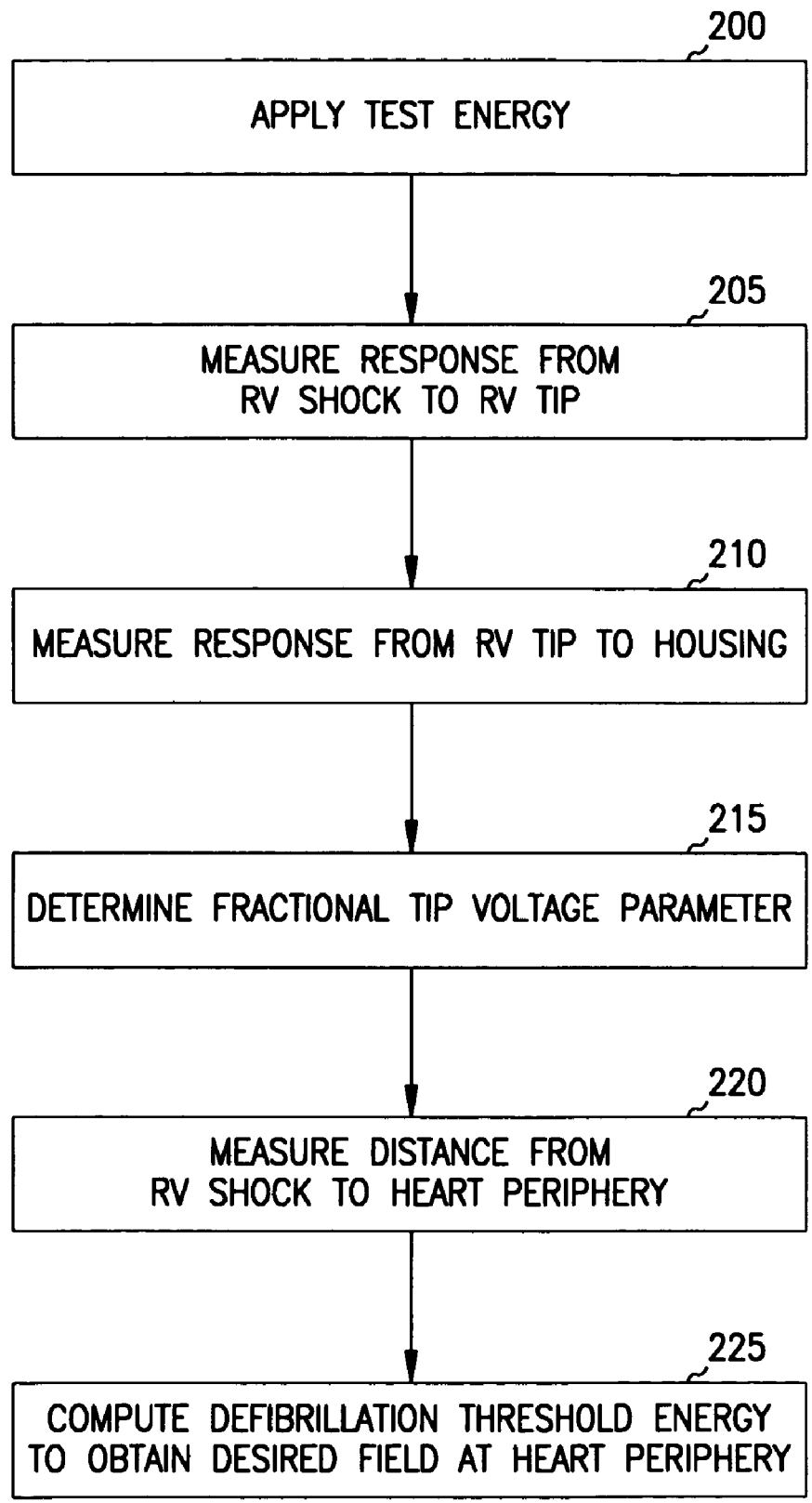
FIG. 2 is a flow chart illustrating a technique for estimating defibrillation thresholds such as using the system of FIG. 1.

FIG. 2 is a flow chart illustrating generally, by way of example, but not by way of limitation, one embodiment of a technique for estimating defibrillation thresholds such as using the system 100 of FIG. 1. This technique is carried out as executable instructions, such as by controller 160, but it need not be carried out in the exact sequence illustrated in FIG. 2. At step 200, test energy module 150 applies a test energy by providing a drive current of predetermined magnitude (e.g., approximately 30 to 1000 microamperes, inclusive) between RV shock electrode 125 and housing electrode 140. In one example, this drive current is delivered in a continuous or pulsed/strobed 25 kHz waveform; in this example the 30 to 1000 microamperes current magnitudes are the zero-to-peak values of this test waveform. However, it is understood that the technique could use any other test energy that does not defibrillate the associated heart tissue and does not induce fibrillation, such as when the energy is delivered during a cardiac repolarization or by using a non-painful stimulus such as a pacing pulse (e.g., amplitude approximately between 0.1 Volt and 10 Volts, inclusive, duration approximately between 0.05 milliseconds and 10 milliseconds, inclusive). In one embodiment, the test energy typically has an energy less than 10 milliJoules, while typical defibrillation threshold energies are between 1 and 40 Joules. The test energy may be delivered from either a current source or a voltage source.

At step 205, response signal module 155 measures a response voltage V1 between RV shock electrode 125 and RV tip electrode 120. At step 210, response signal module 155 also measures a response voltage V2 between RV tip electrode 120 and housing electrode 140. One such embodiment of providing a test current and sensing a resulting voltage is described in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to Cardiac Pacemakers, Inc., the disclosure of which is incorporated herein by reference in its entirety, including its incorporation by reference of Hauck et al., U.S. Pat. No. 5,318,597 entitled "RATE ADAPTIVE CARDIAC RHYTHM MANAGEMENT DEVICE CONTROL ALGORITHM USING TRANS-THORACIC VENTILATION, also assigned to Cardiac Pacemakers, Inc. Although the Hartley et al. patent is directed toward providing a test current and sensing a resulting voltage to measure transthoracic impedance, those same techniques and structures for carrying out such techniques, including the use of a continuous or pulsed/strobed high frequency carrier signal (e.g., at a frequency that is approximately between 1 kHz and 100 kHz, inclusive), are also applicable here. Such techniques are employed either using the electrode configuration illustrated in FIG. 1, or using the electrode configuration described or incorporated by reference in the Hartley et al patent, or by using any other suitable electrode configuration that disposes electrodes for association with heart 115 for providing a test signal and/or detecting a response signal.

In this example, at step 215, a fractional tip voltage parameter V2/(V1+V2) is determined by controller 160 or external programmer 170. This fractional tip voltage parameter provides a measured indication of the electric field distribution near RV shock electrode 125, because it relates to a voltage drop over a known distance d1.

In this example, at step 220, the attending physician or other user measures a distance d2 from the RV shock electrode the outer periphery of the left ventricular apex. In one embodiment, this distance is measured by viewing an image of the heart on a fluoroscope or other imaging apparatus, using the known distance d1 to assess the distance d2. Based on the distance d2 and the fractional tip voltage parameter, a defibrillation threshold is estimated, at step 225, using a model of electric field distribution (for example, having foci at RV shock electrode 125 and at SVC electrode 130, as illustrated in this example by the elliptical lines superimposed on heart 115 in FIG. 1) that provides a desired electric field magnitude throughout the heart, including its periphery.

In one embodiment, a generalized electric field distribution for the particular lead electrode configuration is calculated a priori using the known lead electrode geometry and the boundary element method, or similar method, to solve the electric field Laplace equation. In one example, commercially available finite element analysis software is used to solve the electric field distribution for the particular electrode arrangement. A resulting generalized equation describing the electric field is then obtained using a cubic fit. For a particular electrode configuration, the measured voltage at tip electrode 120 may be different from that obtained from the generalized electric field equation for the modeled electrode geometry, for example, because of a small variation in the distance between tip electrode 120 and coil electrode 125, and/or because of the particular tissue and/or blood conductivity characteristics of the patient. To obtain additional accuracy, these small variations are accounted for by scaling or otherwise calibrating the generalized electric field equation such that it obtains substantially the same electric field at the tip electrode 120 as the measured electric field at tip electrode 120, an indication of which is given by the fractional tip voltage parameter. Using the resulting calibrated electric field equation and measured distance to the heart periphery, the electric field obtained at the heart periphery in response to the test voltage is calculated. The defibrillation threshold voltage, then, is calculated by scaling the test voltage delivered at coil electrode 125 by the ratio of the desired electric field at the heart periphery needed for successful defibrillation (e.g., 5 Volts/cm) to the extrapolated value of electric field at the heart periphery obtained from the calibrated electric field equation in response to the test voltage stimulus.

In this example, it has been assumed that a minimum electric field magnitude of 5 Volts/cm at the left ventricular periphery of heart 115 (at a distance d2 away from RV shocking electrode 125) is required to convert ventricular fibrillation into a normal heart rhythm (e.g., with a 50% probability). A more conservative user might select a larger predetermined desired electric field intensity (e.g., 6 V/cm) at the heart periphery. Moreover, other experimental data might indicate that a lower electric field intensity (e.g., 4 V/cm) is sufficient to obtain a successful defibrillation. It is understood that the present system and techniques are applicable and may be used in conjunction with any desired electric field intensity at the distal point (from the defibrillation electrode) of the tissue being defibrillated.

For ease of use, such as in an implantable device, the defibrillation threshold voltage is, in one embodiment, stored in a lookup table in a memory device. FIG. 3 illustrates generally, by way of example, but not by way of limitation, one embodiment of such a lookup table. In this embodiment, the defibrillation threshold voltage needed to obtain a 5 Volts/cm electric field at the left ventricular heart periphery is given as a function of: (1) the measured distance d2 less the known distance d1; and (2) the fractional tip voltage parameter. Thus, the lookup table in FIG. 3 represents solving the electric field distribution for a particular lead geometry and a range of various heart sizes, calibrating the resulting cubic-fitted electric field equations according to different measured values of electric field as indicated by the range of fractional tip voltage parameters, and obtaining the corresponding defibrillation threshold voltage by scaling the test voltage by the ratio of the "safe" value of electric field at the heart periphery to the extrapolated value of the electric field at the heart periphery as obtained from the calibrated electric field equation in response to the test voltage delivered from the defibrillation coil electrode 120. Thus, FIG. 3 indicates, for example, for a measured distance, (d2−d1), of 3.4 cm and a fractional tip voltage parameter of 45.0, then the predicted defibrillation threshold voltage given by the table in FIG. 3 is 408 Volts.

In this way, the detected electric field (represented by the fractional tip voltage parameter) associated with the detected voltage between RV shock electrode 125 and SVC electrode 130 in response to the test energy is scaled upward to ensure an adequate minimum electric field at the heart periphery (and, therefore, an adequate electric field throughout that portion of the heart tissue being defibrillated). The associated scaled voltage that provides the desired electric field at the heart periphery is deemed the appropriate defibrillation threshold voltage.

Stated differently, in summary, for a given defibrillation waveform, the corresponding defibrillation threshold voltage is obtained as follows. An elliptical or other (e.g., spherical, quadratic, exponential, polynomial, or other approximation of electric field) electric field model is used to extrapolate the electric field at a distal portion of the heart tissue to be defibrillated (e.g., the left ventricular periphery in this example) based on the electric field measured near the defibrillation electrode (e.g., the RV shock electrode 125 in this example) and the measured distance d2 to the distal portion of the heart tissue to be defibrillated. The defibrillation threshold is obtained by scaling the measured voltage at the defibrillation electrode by the ratio of the desired defibrillation electric field at the distal portion of the heart to be defibrillated to the test value of electric field at that distal portion as obtained by the previous measurement and modeled extrapolation. For this particular example, then, the estimated defibrillation threshold voltage, VDFT, is represented by $VDFT = V_{125} * (E_{LV,DESIRED}/E_{LV,MODEL})$; in this equation, $V_{125}$ is the voltage measured (or calculated) at RV shock electrode 125 in response to the test current, $E_{LV,DESIRED}$ is the desired electric field at the left ventricular periphery for proper defibrillation (in this case, assumed to be 5 V/cm), and $E_{LV,MODEL}$ is the electric field at the left ventricular periphery based on the electric field measurement near RV shock electrode 125 and the extrapolation over the distance d2 using the elliptical or other electric field model.

It should be understood that the defibrillation threshold voltage could further be scaled upward to provide a safety margin of additional defibrillation energy. Moreover, although this example described measuring d2 from the RV shocking electrode 125 to the left ventricular periphery, it is understood that the measurement d2 may be performed between any electrode used to deliver defibrillation energy to any portion of heart 115 and a distal portion of the heart tissue that is farthest from the defibrillation electrode but for which an adequate defibrillation electric field is desired.

EXAMPLE B

Figure 4:
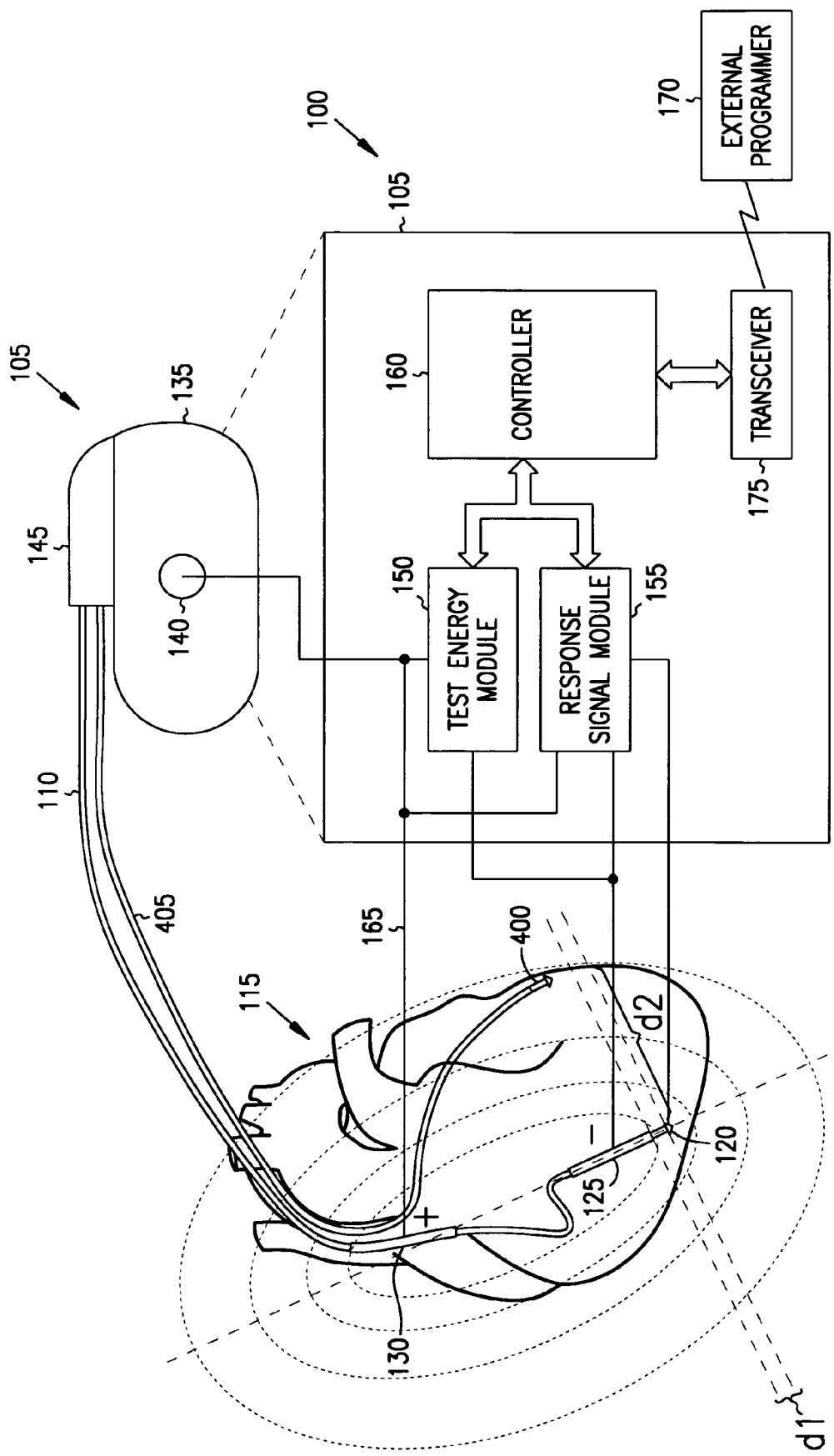
FIG. 4 is a schematic/block diagram illustrating an alternative embodiment of portions of the present cardiac rhythm management system that determines a distance from the defibrillation electrode without requiring fluoroscopic or other imaging.

FIG. 4 is a schematic/block diagram illustrating generally, by way of example, and not by way of limitation, another embodiment of portions of system 100 providing an alternate embodiment of determining the distance d2, such as described with respect to step 220 of FIG. 2, that does not require the use of fluoroscopic or other imaging. FIG. 4 includes an additional peripheral electrode 400 located at or close to the peripheral portion of the left ventricle (a distance d2 away from RV shock electrode 125) at which the predetermined electric field magnitude (e.g., 5 Volts/cm, as in the previous example) is desired during defibrillation. In one embodiment, this peripheral electrode 400 is introduced into the left ventricular periphery (e.g., coronary sinus and/or great cardiac vein) by an transvascular lead 405 through the right atrium and coronary sinus. In another embodiment, peripheral electrode 400 is a patch-type defibrillation electrode disposed on the exterior portion of the left ventricle. In either case, lead 405 may also include additional electrodes.

Figure 5:
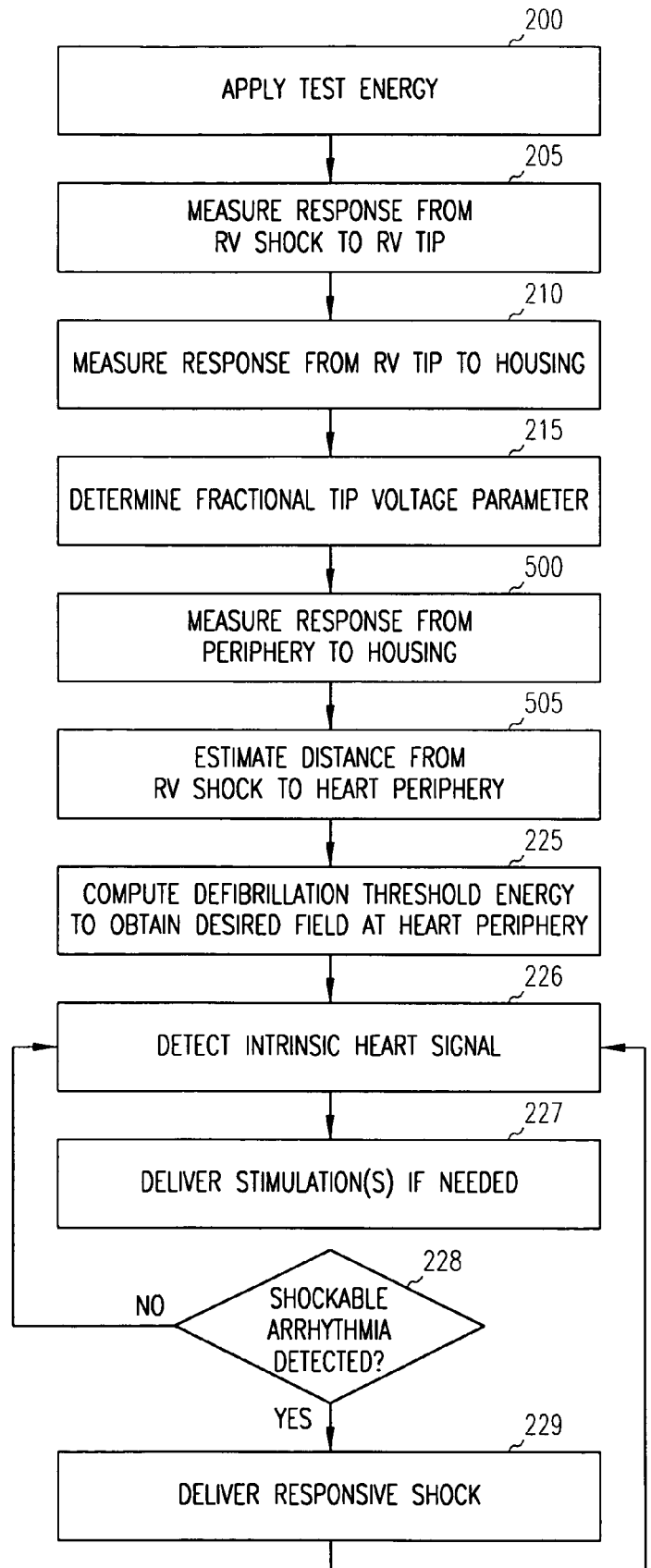
FIG. 5 is a flow chart, similar to that of FIG. 2, illustrating another method of operation such as using the system of FIG. 4.

FIG. 5 is a flow chart, similar to that of FIG. 2, illustrating generally, by way of example and not by way of limitation, another method of operation such as using the embodiment illustrated in FIG. 4. This technique is carried out by executable instructions, such as on controller 160, but it need not be carried out in the exact sequence indicated in FIG. 5. At step 500, an additional voltage measurement V3 is taken between peripheral electrode 400 and housing electrode 140 in response to the current delivered by test energy module 150 at step 200. At step 505 the distance d2 from RV shock electrode 125 to the heart periphery electrode 400 is estimated without relying on fluoroscopic or other imaging techniques to make a measurement. Instead, the distance d2 is estimated using the measured voltage V3 obtained in step 500.

Referring again to FIG. 5, at 226, at least one intrinsic electrical heart signal is detected from a heart of a patient. In one example, this is a ventricular signal that, at least during normal ventricular rhythms, includes QRS complexes indicative of ventricular depolarizations. Such ventricular signals also include discernable characteristics indicative of ventricular tachyarrhythmias, such as a ventricular fibrillation or polymorphic ventricular tachyarrhythmia (PVT) episode to be treated by an electrical shock to the heart. At 227, one or more stimulations are delivered to the heart, if needed to treat a bradyarrhythmia or as part of a cardiac resynchronization therapy (CRT) that is intended to improve spatial coordination of the heart contraction to improve cardiac output. Any such stimulations are delivered at an energy level (e.g., at a pacing-type energy level) that is appropriate to evoke or assist in evoking a responsive heart contraction. At 228, a determination is made of whether a shockable arrhythmia is detected. Examples of a shockable arrhythmia include ventricular fibrillation (VF) or a shockable polymorphic ventricular tachycardia. This detection is performed using a technique having a specificity and a sensitivity, such as from a particular combination of parameters used in detecting the shockable arrhythmia and in delivering/inhibiting shock therapy. In one example, the specificity exceeds the sensitivity. In one example, the determination of whether a shockable arrhythmia exists includes (or, alternatively, consists of) determining whether a ventricular heart rate exceeds a high rate threshold value, such as 220 beats per minute. At 228, if a shockable arrhythmia is detected then, at 229, a shock is delivered in response to the VT/VF, either alone or in combination with one or more other triggers. The shock is intended to terminate the VT/VF such that the heart reverts back to a non-tachyarrhythmic rhythm. Process flow then returns to 226. At 228, if a shockable arrhythmia is not detected, then process flow returns to 226.

Figure 6:
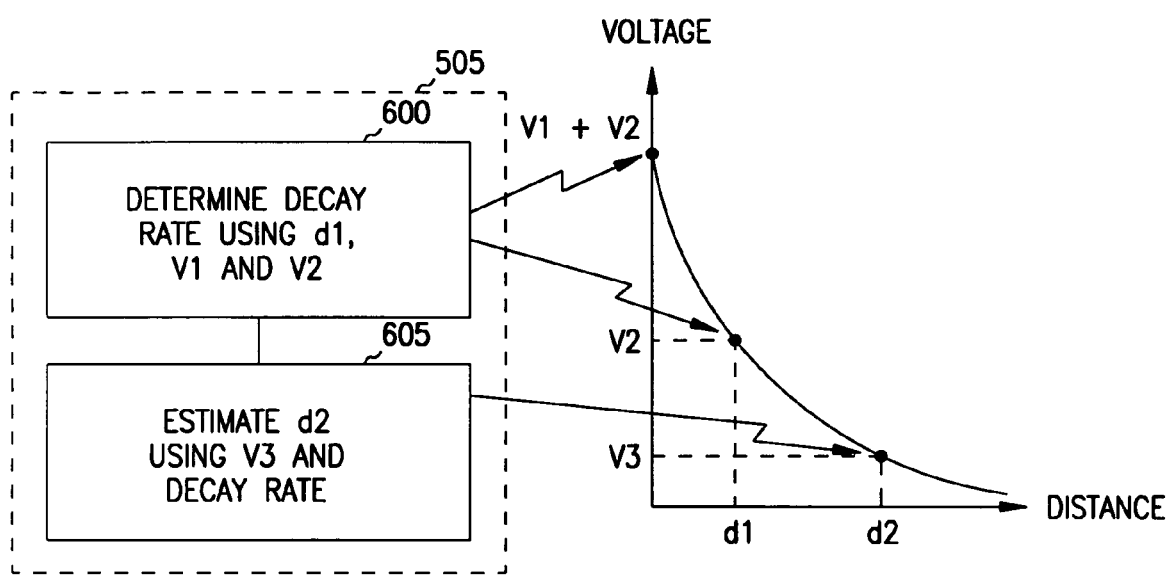
FIG. 6 is a flow chart and accompanying graph illustrating one technique for estimating a distance from an electrode.

FIG. 6 is a flow chart and accompanying graph illustrating generally, by way of example, but not by way of limitation, one technique for estimating the distance d2, at step 505. In this technique, the electric field near RV shock electrode 125 is approximated, as a function of distance, as a decaying exponential, for distances measured radially outward from RV shock electrode 125. By using (V1+V2) and V2 as points on this exponential curve that are separated by the known distance d1, as illustrated in FIG. 6, a decay rate "R" (i.e., the argument of the decaying exponential function) is computed at step 600. Then, at step 605, the distance d2 is estimated using the previously determined decay rate R. Having determined the distance d2 without relying on fluoroscopic imaging techniques, the defibrillation threshold energy is estimated as previously described herein with respect to FIGS. 1-3, or by other suitable technique.

OTHER EXAMPLES

Figure 7:
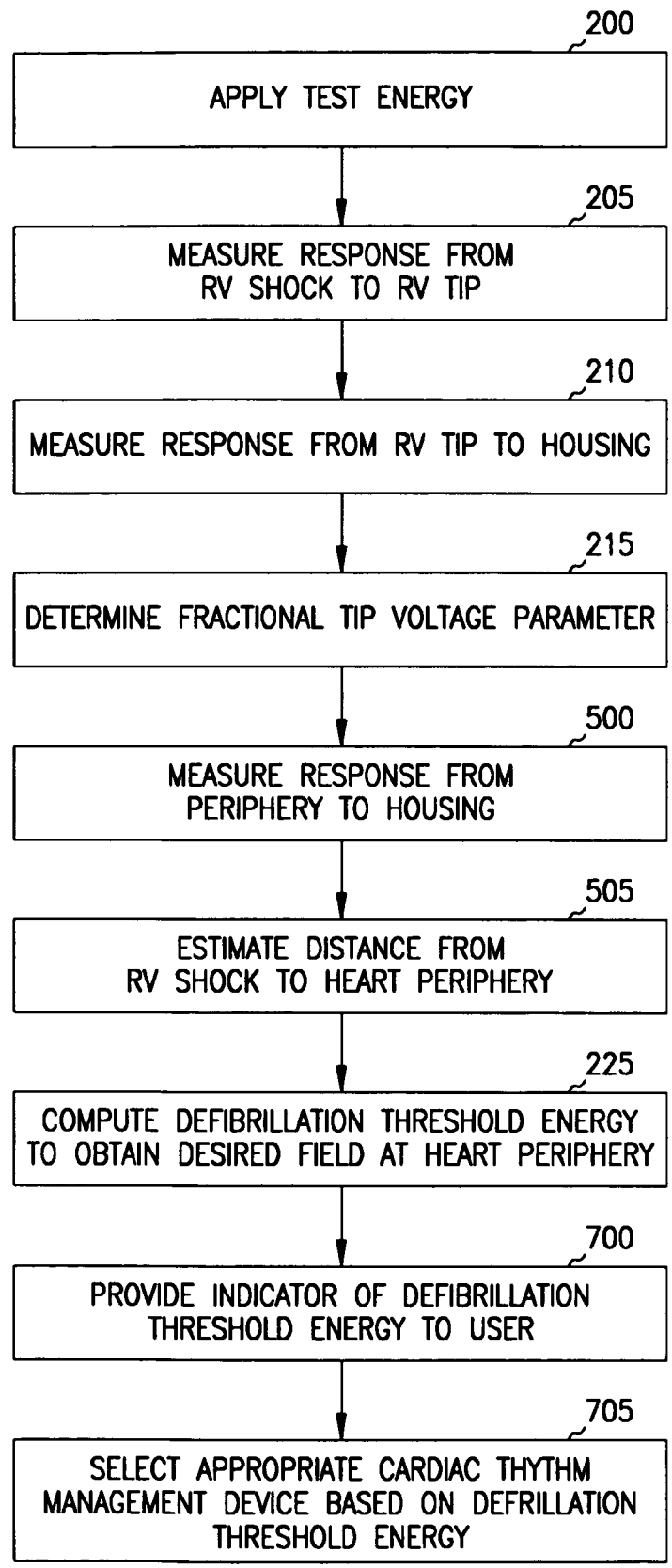
FIG. 7 is a flow chart illustrating another embodiment providing an indicator of the predicted defibrillation threshold and/or selecting an appropriate cardiac rhythm management device for implant.

FIG. 7 is a flow chart illustrating generally, by way of example, but not by way of limitation, another embodiment of using system 100. This embodiment includes steps for estimating defibrillation threshold voltages for a particular defibrillation waveform delivered from a particular electrode configuration, such as described with respect to FIG. 5 (or FIG. 2). Then, at step 700, an indication of the defibrillation threshold energy is provided to the user. In one example, the defibrillation threshold energy estimated within device 105 is communicated by telemetry transceiver 175 to external programmer 170 for display, such as on a computer monitor, audible output, printed means, or using any other indicator. In another example, the defibrillation threshold energy is estimated by hardware included within external programmer 170, which is itself coupled to lead 110 with or without actually implanting a device 105. A resulting indication of the defibrillation threshold energy is displayed on programmer 170. Based on this indicated defibrillation threshold energy, the user selects an appropriate cardiac rhythm management device 105 for implantation. In this way, an implantable cardiac rhythm management device 105 having a larger battery capacity is selected for a patient exhibiting a larger defibrillation threshold voltage than for a patient exhibiting a lesser defibrillation threshold voltage. This selection of a cardiac rhythm management device 105 having appropriate energy capacity may also be based on other factors, including, by way of example, but not by way of limitation, the expected frequency of needed defibrillation episodes, the patient's need for other power-consuming features in the implantable cardiac rhythm management device. Thus, according to this technique of computing defibrillation thresholds for a particular electrode configuration, the user may advantageously determine the appropriate cardiac rhythm management device 105 before actually performing an implantation.

Figure 8:
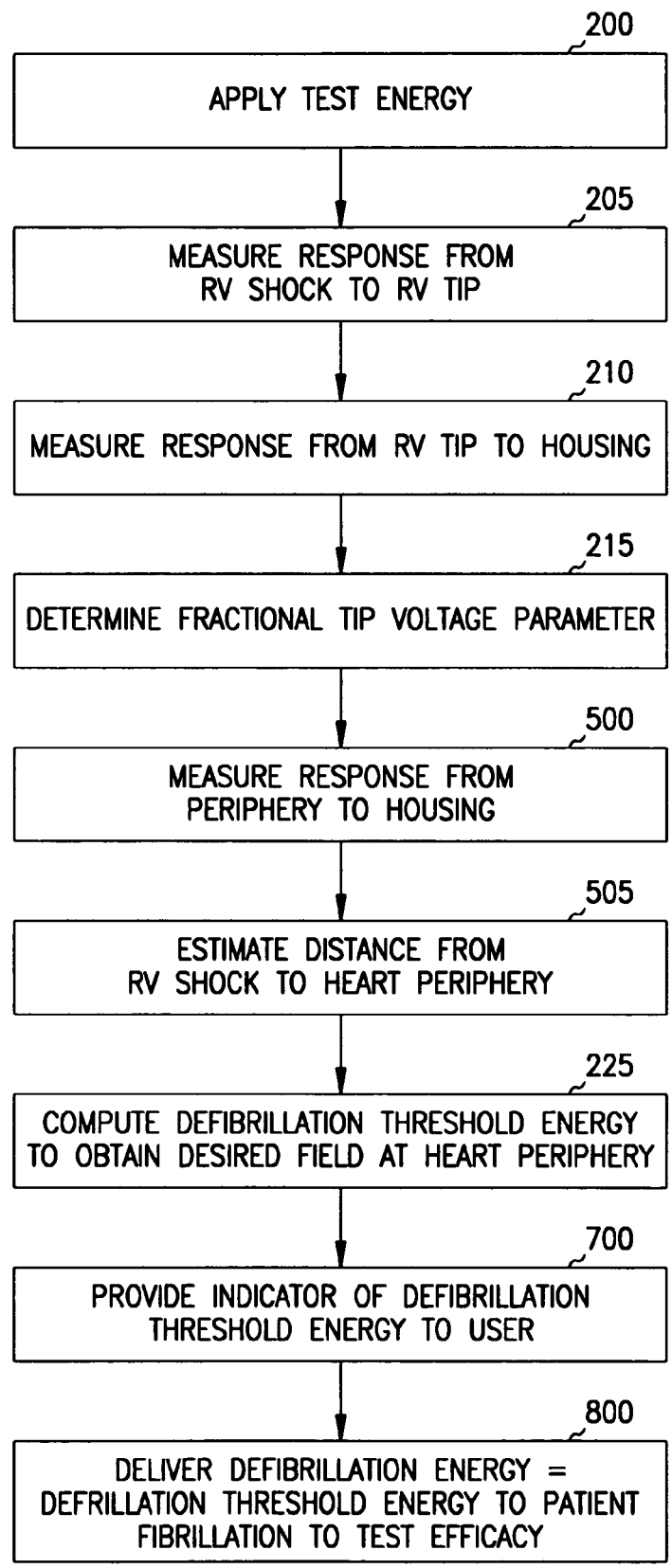
FIG. 8 is a flow chart illustrating another embodiment providing a defibrillation shock based on the predicted defibrillation threshold energy.

FIG. 8 is a flow chart illustrating generally, by way of example, but not by way of limitation, another embodiment of using system 100. This embodiment includes steps for estimating defibrillation threshold voltages for a particular defibrillation waveform and providing an indicator of the defibrillation threshold energy to the user, as described with respect to FIG. 7. Then, at step 800, a defibrillation shock having a magnitude based on the predicted defibrillation threshold energy (e.g., equal to the predicted defibrillation threshold energy) is delivered to a patient in fibrillation to test whether the applied defibrillation shock magnitude is sufficient to defibrillate the patient. If the defibrillation is successful, the user may again test efficacy using a lesser defibrillation shock; if the defibrillation is not successful, the user may again test efficacy using a greater defibrillation shock.

Figure 9:
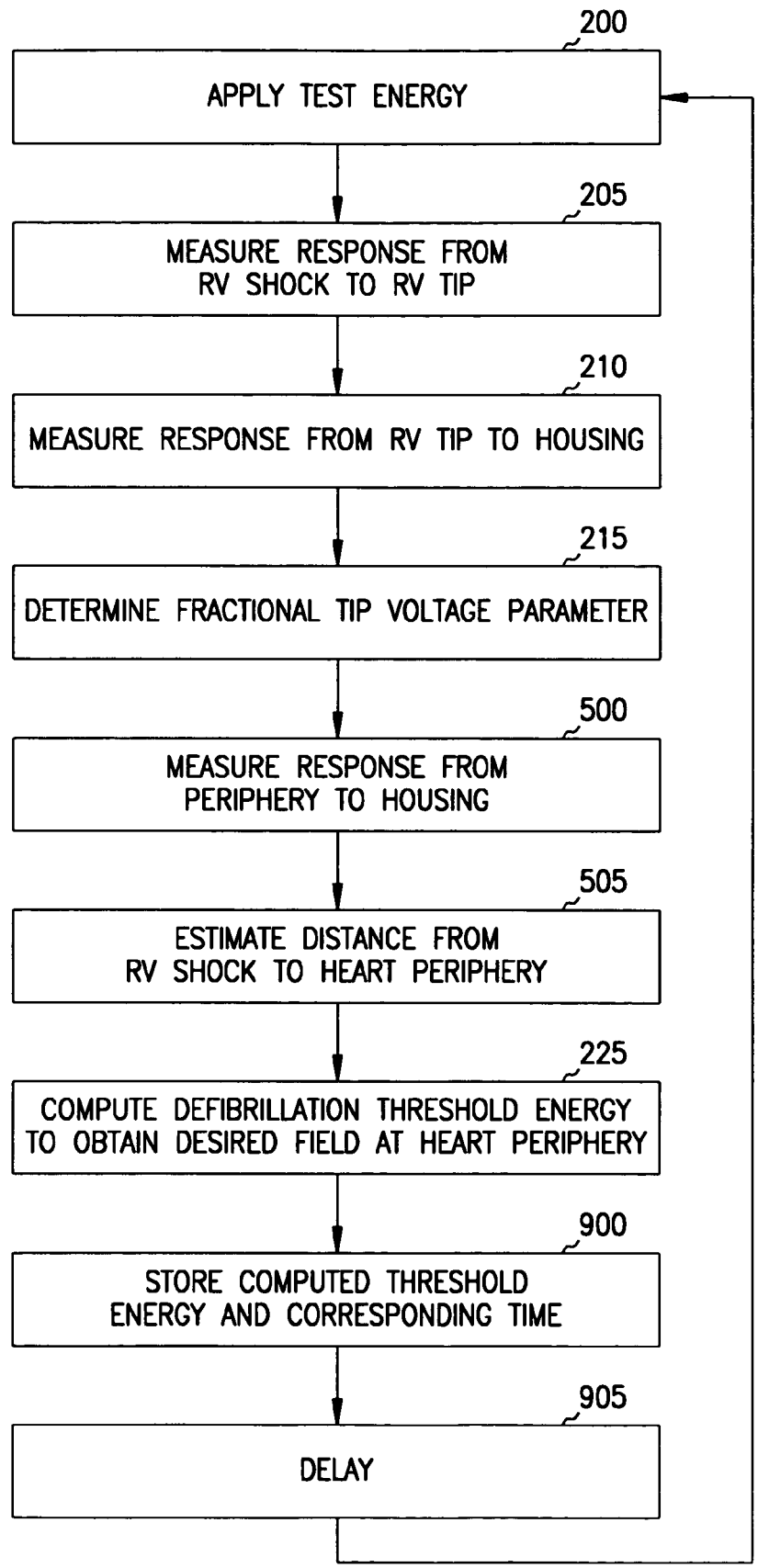
FIG. 9 is a flow chart illustrating another embodiment for recording acute or chronic computed defibrillation thresholds.

FIG. 9 is a flow chart illustrating generally, by way of example, but not by way of limitation, another embodiment of using system 100. This embodiment includes steps for estimating defibrillation threshold voltages for a particular defibrillation waveform (as described with respect to FIGS. 2 and 5). At step 900, the computed defibrillation threshold energy and corresponding time is stored in memory in controller 160. After a delay at step 905, the defibrillation threshold estimation steps are repeated and the resulting defibrillation threshold energy and time are again recorded and stored. The stored defibrillation threshold energy and corresponding time data is, in one embodiment, communicated to external programmer 170 by transceiver 175. In one embodiment, a relatively short delay (e.g., approximately between 1 hour and 1 day, inclusive) is used at step 905, during a period of time immediately following implantation of defibrillation lead 110. In this way, acute changes in defibrillation threshold are monitored and stored. In another. embodiment, a longer delay (e.g., approximately between 1 day and 1 month, inclusive) is used at step 905. In this way, chronic changes in defibrillation threshold are monitored and stored. Such chronic changes in defibrillation threshold provide one indication of patient well-being and suitability for continued use of the cardiac rhythm management system 100.

Figure 10:
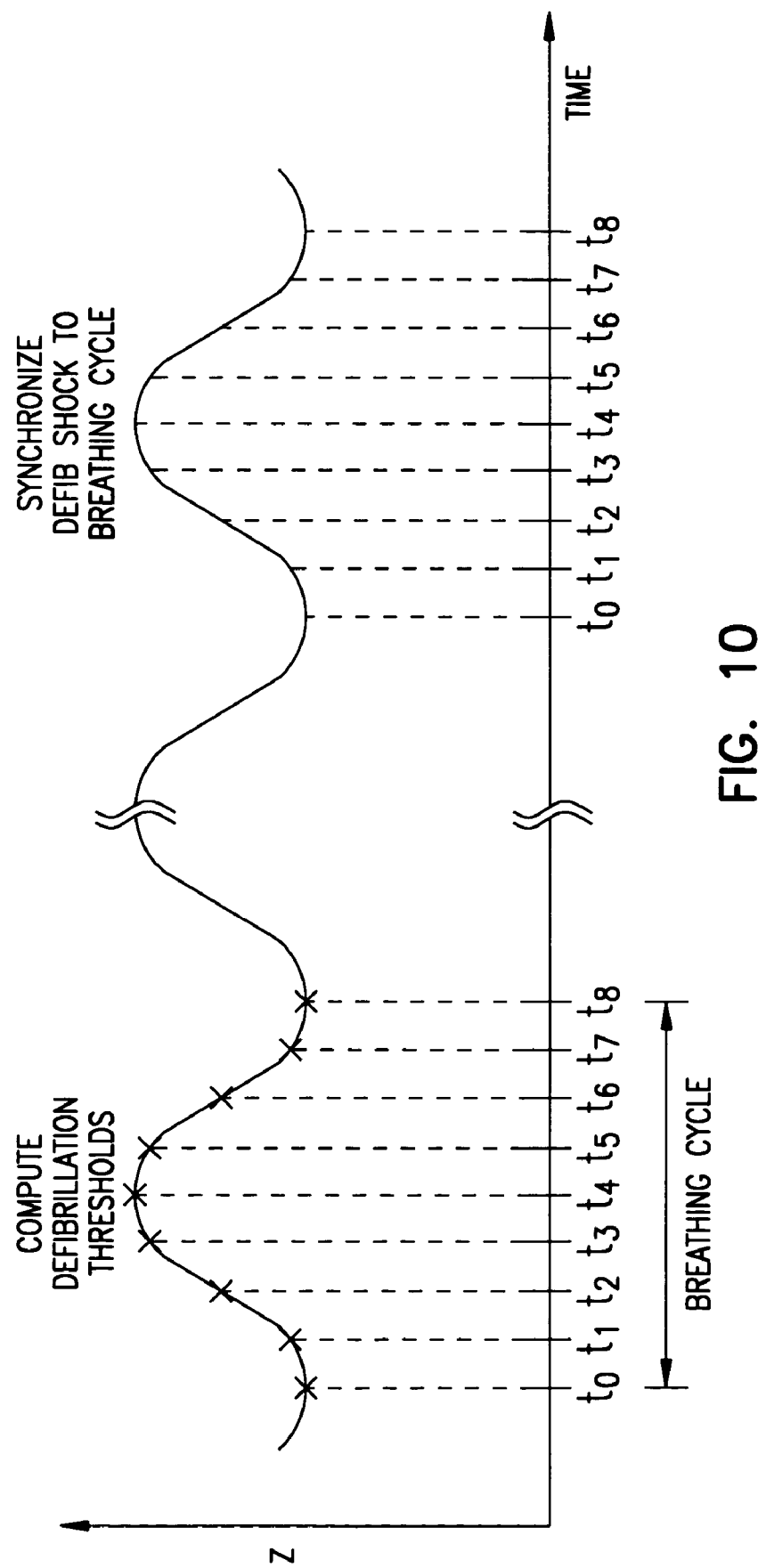
FIG. 10 is a flow chart illustrating another embodiment for modifying the delivery of a defibrillation shock or other therapy based on previously acquired defibrillation threshold data over a range of another patient characteristic.

FIG. 10 is a graph of transthoracic impedance (Z) versus time. FIG. 10 illustrates another aspect of the present system 100 in which a patient characteristic, such as breathing (also referred to as respiration or ventilation) is monitored. One technique for monitoring breathing is by measuring transthoracic impedance, as described in Hartley et al. U.S. Pat. No. 6,076,015 entitled "RATE ADAPTIVE CARDIAC RHYTHM MANAGEMENT DEVICE USING TRANSTHORACIC IMPEDANCE," assigned to Cardiac Pacemakers, Inc., which is incorporated herein by reference in its entirety. As illustrated in FIG. 10, defibrillation thresholds are repeatedly computed, according to the techniques described herein, at several different times during the patient's breathing cycle of inhaling and exhaling. An indication of the portion of the breathing cycle that corresponds to the lowest computed defibrillation threshold is recorded. In one example, this is implemented by recording a transthoracic impedance corresponding to the lowest defibrillation threshold. In another embodiment, this is implemented by recording a time delay from a fiducial point of the thoracic impedance waveform (e.g., maxima, minima, "zero"-crossing, etc.). Then, at some later time when the patient is in fibrillation, a defibrillation shock is delivered by system 100 synchronized to (among other things) the portion of the respiration cycle that was found to correspond to the lowest defibrillation threshold energy. In a broader sense, because the defibrillation threshold estimation techniques disclosed herein do not require an actual defibrillation energy or fibrillation-inducing energy, such defibrillation threshold estimation can be carried out repeatedly for evaluation over a range of any other patient characteristics (e.g., posture, etc.) besides breathing. Variations in the defibrillation threshold energy may then be used to synchronize delivery of the defibrillation shock to that particular patient characteristic, or to otherwise modify therapy delivery.

CONCLUSION

The above-discussed system provides, among other things, an apparatus and methods for estimating defibrillation thresholds without having to induce an arrhythmia or provide a defibrillation shock, and thereby avoids the disadvantages associated therewith, as discussed above. Although the system has been so described to illustrate this one of its advantages, it is not limited in this way. Stated differently, the system could also be used in conjunction with techniques that induce arrhythmias and/or deliver defibrillation countershocks to determine defibrillation thresholds.

The above-discussed system has been particularly described in terms of its use to determine ventricular defibrillation thresholds. However, it is understood that the described technique could also be used to determine atrial or other defibrillation thresholds by simply repositioning the electrodes to be associated with the atrial tissue to be defibrillated. Moreover, the described system need not be confined to a use in determining defibrillation thresholds; it could also be used for determining the required applied voltage at any electrode that is needed to obtain a desired electric field at a distance away therefrom.

The systems and methods described herein for painlessly estimating a defibrillation threshold will be particularly useful in a cardiac rhythm management device having both bradyarrhythmia pacing therapy and defibrillation shock therapy capabilities, where the device is configured to be used in a patient population that is not normally indicated for an anti-tachyarrythmia therapy device. In such patients, erroneously or unnecessarily delivering a defibrillation shock is particularly undesirable, as explained in the above-incorporated U.S. patent application Ser. No. 10/921,777. However, including defibrillation capability in such devices is still useful for preventing patient mortality. Therefore, such devices in such a patient population are particularly well-suited for the present systems and methods of painlessly estimating a defibrillation threshold, since the present systems and methods avoid any need to actually deliver a defibrillation shock during defibrillation threshold testing.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the term "including" is used as being equivalent to the term "comprising," and its interpretation should not be limited to "physically including" unless otherwise indicated.

What is claimed is:

1. An apparatus comprising:
    a test energy circuit adapted to deliver a test energy to a heart of a patient;
    a response signal circuit adapted to detect responding signals providing for an indication of an electric field strength in a predetermined cardiac region, the responding signals resulting from the delivery of the test energy;
    a controller in communication with the test energy circuit and the response signal circuit, the controller adapted to estimate a defibrillation threshold based on the indication of the electric field strength;
    a heart signal sensing circuit to sense intrinsic electrical heart signals from the heart of a patient;

a ventricular tachyarrhythmia/fibrillation detector circuit, operatively coupled to the heart signal sensing circuit, the ventricular tachyarrhythmia/fibrillation detector circuit operable to detect a ventricular tachyarrhythmia/fibrillation, wherein the ventricular tachyarrhythmia/fibrillation detector circuit has a sensitivity and a specificity, and wherein the ventricular tachyarrhythmia/fibrillation detector circuit is configured such that the specificity exceeds the sensitivity;

a defibrillation shock circuit, coupled to the ventricular tachyarrhythmia/fibrillation detector circuit, the defibrillation shock circuit configured to deliver a defibrillation shock in response to the detected ventricular tachyarrhythmia/fibrillation, the defibrillation shock selected to exceed the estimated defibrillation threshold; and a stimulation circuit, coupled to the heart signal sensing circuit, the stimulation circuit configured to deliver to the heart a stimulation at an energy level appropriate to evoke or assist in evoking a responsive heart contraction.

2. The apparatus of claim 1, wherein the test energy circuit includes at least a portion of the defibrillation shock circuit.

3. The apparatus of claim 1, wherein the test energy circuit includes at least a portion of the stimulation circuit 4. The apparatus of claim 1, wherein the response signal circuit includes at least a portion of the heart signal sensing circuit.

5. The apparatus of claim 1, in which the specificity is greater than or equal to 99%.

6. The apparatus of claim 5, in which the sensitivity is less than 99%.

7. The apparatus of claim 5, in which the specificity is greater than or equal to 99.5%.

8. The apparatus of claim 7, in which the sensitivity is less than 99.5%.

9. The apparatus of claim 1, in which the ventricular tachyarrhythmia/fibrillation detector circuit includes one or more shock control modules to determine whether a patient should be shocked, wherein the one or more shock control modules are individually or collectively programmable by one or more parameters, and wherein the one or more parameters are factory programmed to one or more corresponding default values such that the specificity exceeds the sensitivity in a target patient population.

10. The apparatus of claim 1, wherein:
the response signal circuit is configured to determine an indication of a first electric field strength near a first cardiac location from which the test energy is delivered, the first electric field strength resulting from the delivery of the test energy; and the response signal circuit is configured to estimate a second electric field strength, near a second cardiac location, using the indication of the first electric field strength, the second electric field strength associated with a threshold voltage, the second electric field strength resulting from the delivery of the test energy.

11. The apparatus of claim 10, wherein the test energy circuit is configured to deliver a test signal having a test voltage, and wherein the controller is configured to calculate the threshold voltage by scaling the test voltage by a ratio of a predetermined minimum electric field strength to the estimated second electric field strength.

12. The apparatus of claim 1, wherein the apparatus comprises one or more factory-programmed shock control parameters such that the specificity exceeds the sensitivity in a target patient population.

* * * * *

UNITED STATES PATENT AND TRADEMARK OFFICE
CERTIFICATE OF CORRECTION

| | | |
|---|---|---|
| PATENT NO. | : 7,643,877 B2 | Page 1 of 1 |
| APPLICATION NO. | : 11/061315 | |
| DATED | : January 5, 2010 | |
| INVENTOR(S) | : Richard M. Dujmovic et al. | |

It is certified that error appears in the above-identified patent and that said Letters Patent is hereby corrected as shown below:

Title Pg, Item (75), in "Inventors", delete "Pittsburg," and insert -- Pittsburgh, --, therefor.

Title Pg, Item (75), in "Inventors", delete "Oakdale," and insert -- Woodbury, --, therefor.

Title Pg, Item (63), under "Related U.S. Application Data", delete "Continuation-in-part of application No. 09/808,419," and insert -- Continuation of application No. 09/808,419, --, therefor.

Title Page, Item (63), under "Related U.S. Application Data", delete "continuation of application No. 10/744,991," and insert -- continuation-in-part of application No. 10/744,991, --, therefor.

In column 12, line 67, in Claim 1, delete "a" and insert -- the --, therefor.

In column 13, line 25, in Claim 3, after "circuit" insert -- . --.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,643,877 B2
APPLICATION NO. : 11/061315
DATED : January 5, 2010
INVENTOR(S) : Dujmovic, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1182 days.

Signed and Sealed this

Twenty-first Day of December, 2010

David J. Kappos
*Director of the United States Patent and Trademark Office*